(12) United States Patent
Huboux et al.

(10) Patent No.: US 9,758,744 B2
(45) Date of Patent: Sep. 12, 2017

(54) FLORAL, GREEN ODORANT

(71) Applicant: Firmenich SA, Geneva (CH)

(72) Inventors: Alexandre Huboux, Geneva (CH); Robert Moretti, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/309,709

(22) PCT Filed: Apr. 28, 2015

(86) PCT No.: PCT/EP2015/059222
§ 371 (c)(1),
(2) Date: Nov. 8, 2016

(87) PCT Pub. No.: WO2015/169648
PCT Pub. Date: Nov. 12, 2015

(65) Prior Publication Data
US 2017/0145342 A1    May 25, 2017

(30) Foreign Application Priority Data
May 8, 2014 (EP) .................................... 14167524

(51) Int. Cl.
*A61K 8/18* (2006.01)
*C11B 9/00* (2006.01)
*A61Q 15/00* (2006.01)
*A61K 8/34* (2006.01)
*A61Q 13/00* (2006.01)
*C11D 3/50* (2006.01)
*C11D 3/00* (2006.01)

(52) U.S. Cl.
CPC ............ *C11B 9/0015* (2013.01); *A61K 8/342* (2013.01); *A61Q 13/00* (2013.01); *A61Q 15/00* (2013.01); *C11D 3/001* (2013.01); *C11D 3/50* (2013.01)

(58) Field of Classification Search
CPC .............................. A61K 8/342; C11B 9/0015
USPC ............................................................ 512/1
See application file for complete search history.

(56) References Cited

U.S. PATENT DOCUMENTS 2,838,576 A * 6/1958 Normant ................. C07C 29/40
424/63

FOREIGN PATENT DOCUMENTS

DE            2228333 B2    6/1980
WO      WO2010052636 A1    5/2010

OTHER PUBLICATIONS

Molander et al. "Reduction of vinyloxiranes with samarium diiodide. An efficient route to functionalized chiral, nonracemic (E)-allylic alcohols", The Journal of Organic Chemistry, American Chemical Society, US, vol. 51, No. 26, Jan. 1986, pp. 5259-5264.*
International Search Report and Written Opinion, application PCT/EP2015/059222 mailed Sep. 15, 2015.
Molander et al., J. Org. Chem. 1986, 51, 5259-5264.
International Preliminary Report on Patentability, PCT/EP2015/059222, Sep. 15, 2015.

* cited by examiner

*Primary Examiner* — Lanee Reuther
(74) *Attorney, Agent, or Firm* — Winston & Strawn LLP

(57) ABSTRACT

The present invention concerns a composition of matter comprising at least 85% w/w of (Z)-5,9-dimethyldeca-3,8-dien-5-ol and at most 15% w/w of (E)-5,9-dimethyldeca-3,8-dien-5-ol, as well as the use as perfuming ingredient of said composition of matter.

14 Claims, No Drawings

FLORAL, GREEN ODORANT

This application is a 371 filing of International Patent Application PCT/EP2015/059222 filed 28 Apr. 2015, which claims the benefit of European patent application n° 14167524.9 filed 8 May 2014.

TECHNICAL FIELD

The present invention relates to the field of perfumery. More particularly, it concerns a composition of matter comprising at least 85% w/w of (Z)-5,9-dimethyldeca-3,8-dien-5-ol and at most 15% w/w of (E)-5,9-dimethyldeca-3, 8-dien-5-ol. Said composition of matter is a useful perfumery ingredient, and therefore the present invention comprises the invention's compound as part of a perfuming composition or of a perfuming consumer product.

PRIOR ART

To the best of our knowledge, the invention's composition of matter is novel.

However, in the document U.S. Pat. No. 2,838,576 is reported a general formula, encompassing the present composition of matter, which describes compounds useful as perfumery ingredient to confer "bergamot-lavander" odor notes. In said document, there is no mention of specific requirements regarding the double bond configuration, and it is described only an undefined composition of matter of 2,4,8-trimethylnona-2,7-dien-4-ol isomers but which has significantly different odor properties compared to the present composition of matter.

DESCRIPTION OF THE INVENTION

We have now surprisingly discovered that a composition of matter comprising:
at least 85% w/w of (Z)-5,9-dimethyldeca-3,8-dien-5-ol; and
at most 15% w/w of (E)-5,9-dimethyldeca-3,8-dien-5-ol;
the percentage being relative to the total weight of the composition of matter; can be used as perfuming ingredient, for instance to impart odor notes of the floral, green type.

Each compound of the present composition of matter can be in the form of any one of its enantiomers or a mixture thereof. According to a particular embodiment, the composition of matter is in a racemic form.

According to a particular embodiment of the invention, the present composition of matter comprises:
at least 90% w/w of (Z)-5,9-dimethyldeca-3,8-dien-5-ol; and
at most 10% w/w of (E)-5,9-dimethyldeca-3,8-dien-5-ol;
the percentage being relative to the total weight of the composition of matter.

According to a particular embodiment of the invention, the present composition of matter consists of essentially (Z)-5,9-dimethyldeca-3,8-dien-5-ol, i.e. the cis isomer accounts for at least 95% w/w, or even at least 98% or 99% w/w. This compound possesses a nice floral and green notes duality. The floral notes are in the direction of white flower, but with a significant and appreciated violet twist, while the green note is a sparkling and fresh one with a cis-3-hexenol, sage and violet leaves aspect. The odor of this compound does not present any, or significant, citrus-bergamot notes. This compound is particularly appreciated by the person skilled in the art for its floral and green duality to and its ability to impart/maintain a significant lift and volume to a perfuming composition.

The odor character of the invention's composition of matter is very surprising in view of the prior art. Indeed, when the odor of the invention's composition of matter is compared with that of the prior art composition of matter, or with that of 2,4,8-trimethylnona-2,7-dien-4-ol, then the differences are striking, and can be described as in Table 1 herein below.

The present composition of matter is considered by the skilled person in the art as filling a hole in the perfumer palette by providing a sparkling floral/green duality.

TABLE 1

Various isomers and their odor properties

| Compound/composition structure and name | Odor notes |
|---|---|
| (Z)-5,9-dimethyldeca-3,8-dien-5-ol | Floral and green notes with an aromatic twist. No bergamot notes, and no lavender notes. |
| (E)-5,9-dimethyldeca-3,8-dien-5-ol | Gazoline, Chemical, terpenic. No green notes, and no aromatic aspects. |
| Prior art compound: 2,4,8-trimethylnona-2,7-dien-4-ol | Bergamot, lavender, linalyl acetate/ linalool, slight jasmonic aspects. No green notes, and no aromatic aspects. |
| Prior art compound: (E)-4,8-dimethylnona-2,7-dien-4-ol | Bergamot, lavender, linalyl acetate/ linalool, slight jasmonic aspects. No green notes, and no aromatic aspects. |

The (E) isomer of 5,9-dimethyldeca-3,8-dien-5-ol possesses a non-interesting organoleptic profile very different compared to the (Z) isomer. Thus the sage character of 5,9-dimethyldeca-3,8-dien-5-ol is only perceivable when the (E) is in small amount, otherwise the chemical character of the (E) dominates the olfactive profile. Even more surprisingly, neither the (Z) isomer nor the (E) isomer impart the "bergamot-lavander" odor notes reported in U.S. Pat. No. 2,838,576. Said differences lend the invention's composition of matter and the prior art composition of matter to be each suitable for different uses, i.e. to impart different organoleptic impressions.

As mentioned above, the invention concerns the use of the invention's composition of matter as perfuming ingredient. In other words, it concerns a method to confer, enhance, improve or modify the odor properties of a perfuming composition or of a perfumed article, which method comprises adding to said composition or article an effective amount of the invention's composition of matter.

According to a particular embodiment of the invention, said use or method is to impart odor notes of floral, green type.

By "use of the invention's composition of matter" it has to be understood here also the use of any perfuming composition containing the invention's composition of matter and which can be advantageously employed in perfumery industry.

Said perfuming compositions, which in fact can be advantageously employed as perfuming ingredients, are also an object of the present invention.

Therefore, another object of the present invention is a perfuming composition comprising:

i) as perfuming ingredient, the invention's composition of matter as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not invention's composition of matter. Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are to well known to a person skilled in the art.

An invention's composition consisting of the invention's composition of matter and at least one perfumery carrier represents a particular embodiment of the invention as well as a perfuming composition comprising the invention's composition of matter, at least one perfumery carrier, at least one perfumery base, and optionally at least one perfumery adjuvant.

For the sake of clarity, it is also understood that any mixture resulting directly from a chemical synthesis, e.g. a reaction medium without an adequate purification, in which the invention's composition of matter would be involved as a starting, intermediate or end-product could not be considered as a perfuming composition according to the invention as far as said mixture does not provide the inventive composition of matter in a suitable form for perfumery. Thus, unpurified reaction mixtures are generally excluded from the present invention unless otherwise specified.

Furthermore, the invention's composition of matter can also be advantageously used in all the fields of modern perfumery, i.e. fine or functional perfumery, to positively impart or modify the odor of a consumer product into which said invention's composition of matter is added. Consequently, another object of the present invention is represented by a perfuming consumer product comprising, as perfuming ingredient, an invention's composition of matter, as defined above.

The invention's composition of matter can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of at least one invention's composition of matter.

The nature and type of the constituents of the perfumery consumer product do not warrant a more detailed description here, which in any case would not be exhaustive, the skilled person being able to select them on the basis of his general knowledge and according to the nature and the desired effect of said product.

Non-limiting examples of suitable perfumery consumer product can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer products may represent an aggressive medium for the invention's composition of matter, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the composition of matter according to the invention can be incorporated into the various aforementioned articles or compositions vary within a wide range of values. These values are dependent on the nature of the article to be perfumed and on the desired organoleptic effect as well as the nature of the co-ingredients in a given base when the composition of matter according to the invention are mixed with perfuming co-ingredients, solvents or additives commonly used in the art.

For example, in the case of perfuming compositions, typical concentrations are in the order of 0.5% to 40% by weight, or even more, of the invention's composition of matter based on the weight of the composition into which they are incorporated. Concentrations lower than these, such as in the order of 0.01% to 4.0% by weight, can be used when said the invention's composition of matter is incorporated into perfumed articles, percentage being relative to the weight of the article.

The invention's composition of matter, and the (Z)-5,9-dimethyldeca-3,8-dien-5-ol essentially pure, can be prepared according to several methods. As reported in the experimental part, one possibility is the addition of but-1-yn-1-yl Grignard such as but-1-yn-1-yl magnesium chloride to 6-methyl-5-hepten-2-one. The triple bond of 5,9-dimethyldec-8-en-3-yn-5-ol obtained is then reduced under appropriate conditions in order to provide selectively (Z)-5,9-dimethyldeca-3,8-dien-5-ol (e.g. Lindlar catalyst). The same intermediate could also be synthesized by the addition of but-1-yne to 6-methyl-5-hepten-2-one under basic conditions as described in DE2228333. Another approach starting from the same starting material as above passes through the acetylene addition providing the 3,7-dimethyloct-6-en-1-yn-3-ol then the ethylation of the triple bond and finally, as previously described, the stereoselective hydrogenation of the triple bond (e.g. Lindlar catalyst) leading to (Z)-5,9-dimethyldeca-3,8-dien-5-ol.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical shifts δ are indicated in ppm with respect to TMS as standard, the coupling constants J are expressed in Hz.

Example 1

Synthesis of the Invention's Composition of Matter

Preparation of a Composition of Matter Comprising at Least 98% of (Z)-5,9-dimethyldeca-3,8-dien-5-ol a) 5,9-dimethyldec-8-en-3-yn-5-ol 50 ml of methyltetrahydrofuran were saturated with butyne. 100 ml of 3M Methylmagnesiumchloride were then added dropwise at 23° C., over 50 minutes and the resulting suspension stirred a further 20 minutes. 36.6 g of methylheptenone were added over 2 hours, while maintaining an atmosphere of butyne over the reaction mixture. The reaction mixture was stirred for a further 2 hours and a dilute aqueous solution of citric acid was added rapidly dropwise with cooling. The resulting aqueous phase was removed and the organic phase washed to neutrality with dilute aqueous sodium citrate. Concentration and vacuum distillation afforded 18.4 g of 99% pure propargylic alcohol (Boiling point: 103° C. at 8 mbar).

$^{13}$C NMR: 12.3 (t), 14.0 (q), 17.7 (q), 23.8 (t), 25.7 (q), 30.2 (q), 43.7 (t), 68.4 (s), 83.2 (s), 85.3 (s), 124.1 (d), 132.2 (s)

$^1$H NMR: 1.14 (t, J=7.5 Hz, 3H); 1.45 (s, 3H); 1.65 (brs, 3H); 1.68-1.63 (m, 2H); 1.70 (brs, 3H); 2.08 (s, 1H); 2.21 (q, J=7.5 Hz, 2H); 2.32-2.12 (m, 2H); 5.17 (mc, 1H)

b) (Z)-5,9-dimethyldeca-3,8-dien-5-ol 18.8 g of 5,9-dimethyldec-8-en-3-yn-5-ol were treated with 71 mg of Lindlar catalyst under 1 atmosphere of hydrogen for 15 hours 30 minutes at 25° C. The reaction mixture was then diluted with ether and filtered. The crude product was concentrated and purified by chromatography on silica gel (elution with heptane/MTBE mixture). Concentration of the desired fractions and distillation gave 5.5 g of 99% pure (E/Z ratio of 0.3/99.7) (Z)-5,9-dimethyldeca-3,8-dien-5-ol (bp 41° C. at 0.3 mbar).

$^{13}$C NMR: 14.6 (q), 17.7 (q), 21.5 (t), 23.0 (t), 25.7 (q), 29.4 (q), 43.5 (t), 74.3 (s), 124.5 (d), 131.8 (s), 133.2 (d), 135.1 (d)

$^1$H NMR: 0.98 (t, J=7.5, 3H); 1.33 (s, 3H); 1.59 (s, 1H); 1.60 (mc, 2H); 1.62 (brs, 3H); 1.69 (brs, 3H); 2.14-2.00 (m, 2H); 2.32 (mc, 2H); 5.14 (tqq, J=7.2/1.4/1.4 Hz, 1H); 5.38-5.32 (m, 2H)

Example 2

Preparation of a Perfuming Composition

A perfuming composition for shampoos, of the chamomile type, was prepared by admixing the following ingredients:

| Parts by weight | Ingredient |
|---|---|
| 600 | Benzyl acetate |
| 50 | Cyclanol acetate |
| 100 | Styrallyl acetate |
| 50 | Aladinate ® [1] |
| 500 | Hexylcinnamic aldehyde |
| 150 | 10%* Aldolone ® [1] |
| 50 | 10%* Methyl anthranilate |
| 40 | Methyl benzoate |
| 50 | Ethyl (Z)-2,4-dimethyl-2-pentenoate |
| 100 | Camphor |
| 60 | Carvone Laevo |
| 50 | Citronellyl Nitrile |
| 20 | Allyl cyclohexylpropionate |
| 50 | Dihydroestragol |
| 1000 | Dihydromyrcenol |
| 100 | Eucalyptus essential oil |
| 100 | Eugenol |
| 250 | Exaltolide ® [2] |
| 80 | 10%* Gamma Undecalactone |
| 100 | Geraniol |
| 250 | Granny Smith [a] |
| 500 | Hedione ® [4] |
| 50 | Allyl heptanoate |
| 50 | Hivernal ® [5] |

-continued

| Parts by weight | Ingredient |
|---|---|
| 50 | Iralia ® 6) Total |
| 500 | 2-Phenoxyethyl isobutyrate |
| 250 | Lilial ® 7) |
| 300 | Lorysia ® 8) |
| 20 | Methylparacresol |
| 150 | 10%* Muscenone ™ 9) Delta |
| 20 | 10%* Methyl octinecarbonate |
| 600 | Phenethylol |
| 50 | 1%* Pyrazobutyle |
| 250 | Sclareolate ® 10) |
| 200 | Terpineol |
| 100 | 2-Ethyl-4,4-dimethylcyclohexanone |
| 40 | (2,2-Dimethoxyethyl)benzene |
| 120 | 2,4-Dimethyl-3-cyclohexene-1-carbaldehyde |
| 7000 | |

*in dipropyleneglycol
1) 3-methyl-2-hexenyl acetate; origin: Firmenich SA, Geneva, Switzerland
2) 7-propyl-2H,4H-1,5-benzodioxepin-3-one; origin: Firmenich SA, Geneva, Switzerland
3) pentadecanolide; origin: Firmenich SA, Geneva, Switzerland
4) methyl dihydrojasmonate; origin: Firmenich SA, Geneva, Switzerland
5) 3-(3,3/1,1-dimethyl-5-indanyl)propanal; origin: Firmenich SA, Geneva, Switzerland
6) mixture of methylionones isomers; origin: Firmenich SA, Geneva, Switzerland
7) 3-(4-tert-butylphenyl)-2-methylpropanal; origin: Givaudan SA, Vernier, Switzerland
8) 4-(1,1-dimethylethyl)-1-cyclohexyl acetate; origin: Firmenich SA, Geneva, Switzerland
9) 3-methyl-5-cyclopentadecen-1-one; origin: Firmenich SA, Geneva, Switzerland
10) propyl (S)-2-(1,1-dimethylpropoxy)propanoate; origin: Firmenich SA, Geneva, Switzerland
a) Compounded specialty; origin: Firmenich SA, Geneva, Switzerland The addition of 3000 parts by weight of the invention's composition of matter described in example 1 to the above-described perfuming composition imparted a fresh floral, green aspect which reinforced the chamomile note of the original composition.

When instead of invention's composition was added the same amount of the prior art (E)-4,8-dimethyl-2,7-nonadien-4-ol, the new fragrance was clearly lavender/bergamot much less chamomile.

When instead of invention's composition was added the same amount of the prior art 2,4,8-trimethylnona-2,7-dien-4-ol, the new fragrance was clearly citrusy/bergamot and less sparkling.

When instead of the invention's composition was added the same amount of linalool, the new fragrance was a bit more floral (but less than with the invention composition), but also less chamomile and lavender.

Example 3

Preparation of a Perfuming Composition

A perfuming composition, of the citrus grapefruit type, was prepared by admixing the following ingredients:

| Parts by weight | Ingredient |
|---|---|
| 50 | Isobornyl acetate |
| 50 | Geranyl acetate |
| 10 | Fenchylic alcohol |
| 40 | C 10 aldehyde |
| 60 | C 8 aldehyde |
| 30 | C 9 aldehyde |
| 20 | MNA aldehyde |
| 100 | Lemon essential oil |
| 100 | Citronellol |
| 200 | Citronellyl Nitrile |
| 30 | Citronnella oil |
| 10 | Damascenone |
| 60 | Delphone ™ 1) |
| 60 | Delta Damascone |

-continued

| Parts by weight | Ingredient |
|---|---|
| 40 | Doremox ® 2) |
| 220 | Eucalyptol |
| 30 | Eugenol |
| 1250 | Geraniol |
| 350 | Hedione ® 3) |
| 30 | Hivernal ® 4) |
| 500 | Iso E ® 5) Super |
| 30 | Methylheptenone |
| 20 | Methylnaphthylcetone |
| 40 | (1'R)-2-[2-(4'-methyl-3'-cyclohexen-1'-yl)propyl]cyclopentanone |
| 40 | 10%* Neobutenone ® 6) Alpha |
| 40 | Paracymene |
| 1200 | Phenethylol |
| 250 | Salicynile ® 7) |
| 250 | Sclareolate ® 8) |
| 40 | 10%* (4Z)-4-dodecenal |
| 200 | Orange essential oil |
| 300 | Terpineol |
| 100 | Terpinolene |
| 700 | Ionone Beta |
| 50 | 2,4-Dimethyl-3-cyclohexene-1-carbaldehyde |
| 6500 | |

*in dipropyleneglycol
1) 2-pentyl-cyclopentanone; origin: Firmenich SA, Geneva, Switzerland
2) tetrahydro-4-methyl-2-phenyl-2H-pyran; origin: Firmenich SA, Geneva, Switzerland
3) methyl cis-dihydrojasmonate; origin: Firmenich SA, Geneva, Switzerland
4) 3-(3,3/1,1-dimethyl-5-indanyl)propanal; origin: Firmenich SA, Geneva, Switzerland
5) 1-(octahydro-2,3,8,8-tetramethyl-2-naphthalenyl)-1-ethanone; origin: Givaudan SA, Vernier, Switzerland
6) 1-(5,5-dimethyl-1-cyclohexen-1-yl)-4-penten-1-one; origin: Firmenich SA, Geneva, Switzerland
7) (2Z)-2-phenyl-2-hexenenitrile; origin: Firmenich SA, Geneva, Switzerland
8) propyl (S)-2-(1,1-dimethylpropoxy)propanoate; origin: Firmenich SA, Geneva, Switzerland The addition of 3500 parts of the invention's composition of matter described in example 1 to the above-described perfuming composition imparted a clear green tea connotation.

When instead of the invention's composition was added the same amount of linalool, the new fragrance was much more white floral, without the tea aspect.

When instead of invention's composition was added the same amount of the prior art (E)-4,8-dimethyl-2,7-nonadien-4-ol, the new fragrance became lavander and much less grapefruit.

What is claimed is:

1. A composition of matter comprising:
   at least 85% w/w of (Z)-5,9-dimethyldeca-3,8-dien-5-ol; and
   at most 15% w/w of (E)-5,9-dimethyldeca-3,8-dien-5-ol;
   the percentage being relative to the total weight of the composition of matter, wherein the composition of matter imparts floral green odor notes.

2. A composition of matter according to claim 1, characterized in that said composition of matter comprises:
   at least 90% w/w of (Z)-5,9-dimethyldeca-3,8-dien-5-ol; and
   at most 10% w/w of (E)-5,9-dimethyldeca-3,8-dien-5-ol;
   the percentage being relative to the total weight of the composition of matter.

3. A method to confer, enhance, improve or modify the odor properties of a perfuming composition or of a perfumed article, which method comprises adding to said perfuming composition or perfuming article an effective amount of the composition of matter of claim 2.

4. A perfuming composition comprising:
i) the composition of matter of claim 2;
ii) at least one ingredient selected from the group consisting of a perfumery carrier and a perfumery base and
iv) optionally at least one perfumery adjuvant.

5. A perfuming consumer product comprising the composition of matter of claim 2.

6. A composition of matter according to claim 1, characterized in that said composition consists of at least 95% w/w of (Z)-5,9-dimethyldeca-3,8-dien-5-ol.

7. A method to confer, enhance, improve or modify the odor properties of a perfuming composition or of a perfumed article, which method comprises adding to said perfuming composition or perfuming article an effective amount of the composition of matter of claim 6.

8. A perfuming composition comprising
i) the composition of matter of claim 6;
ii) at least one ingredient selected from the group consisting of a perfumery carrier and a perfumery base; and
v) optionally at least one perfumery adjuvant.

9. A perfuming consumer product comprising the composition of matter of claim 6.

10. A method to confer, enhance, improve or modify the odor properties of a perfuming composition or of a perfumed article, which method comprises adding to said perfuming composition or perfuming article an effective amount of the composition of matter of claim 1.

11. A perfuming composition comprising
i) the composition of matter of claim 1;
ii) at least one ingredient selected from the group consisting of a perfumery carrier and a perfumery base; and
iii) optionally at least one perfumery adjuvant.

12. A perfuming consumer product comprising the composition of matter of claim 1.

13. A perfuming consumer product according to claim 12, characterized in that the perfuming consumer product is a perfume, a fabric care product, a body-care product, an air care product or a home care product.

14. A perfuming consumer product according to claim 12, characterized in that the perfuming consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *